US00PP16251P3

(12) United States Plant Patent
Larsen

(10) Patent No.: US PP16,251 P3
(45) Date of Patent: Feb. 14, 2006

(54) *OSTEOSPERMUM* PLANT NAMED 'SUNNY HENRY'

(50) Latin Name: *Osteospermum ecklonis (DC) T. Norl.*
Varietal Denomination: Sunny Henry

(75) Inventor: Bjarne N. Larsen, Odense (DK)

(73) Assignee: Sunny Gronnegyden ApS, Odense (DK)

( * ) Notice: Subject to any disclaimer, the term of this patent is extended or adjusted under 35 U.S.C. 154(b) by 88 days.

(21) Appl. No.: 10/788,298

(22) Filed: Mar. 1, 2004

(65) Prior Publication Data

US 2004/0210975 P1 Oct. 21, 2004

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

GTITM UPOVROM Citation for 'Sunny Henry' as per QZ PBR 020996; Jul. 3, 2002.*

* cited by examiner

*Primary Examiner*—Kent Bell
(74) *Attorney, Agent, or Firm*—Foley & Lardner, LLP

(57) ABSTRACT

A new distinct cultivar of *Osteospermum* plant named 'Sunny Henry', characterized by white ray floret color 158D with slight green-yellow tinge, RHS 1B, to pure white, RHS 155D; dense and bushy plant form, mainly due to upright stems; vigorous growth habit; less need for chemical growth retardation; and high number of inflorescences per plant.

4 Drawing Sheets

Genus and species of the plant claimed: *Osteospermum ecklonis* (*DC*) *T Norl.*
Variety denomination: 'Sunny Henry'.

BACKGROUND OF THE INVENTION

The present Invention relates to a new and distinct cultivar of *Osteospermum* plant, botanically known as *Osteospermum ecklonis* (*DC*) *T Norl.*, commonly known by the name Cape Daisy, and hereinafter referred to by the name 'Sunny Henry'.

The new *Osteospermum* is a product of a planned breeding program conducted by the Inventor, Bjarne N. Larsen, in Stige, Denmark. The new *Osteospermum* originated from a cross made in 2000 by the Inventor between *Osteospermum ecklonis* (*DC*) *T. Norl.* designated '1.154.93' (unpatented) and *Osteospermum ecklonis* (*DC*) *T. Norl.* variety name 'Sunny Alex' (unpatented). The Inventor selected the new *Osteospermum* cultivar from the progeny of the above crossing in 2002 on the basis of its inflorescence color and compact, freely branching habit. Plants of the new *Osteospermum* are upright, compact and have a unique color combination of upper and underside of the rayflorets.

Asexual reproduction of the new cultivar by terminal vegetative cuttings taken and propagated during trial production batches in Stige, Denmark, has shown that the unique features of this new *Osteospermum* are stable and reproduced true to type in many successive generations.

BRIEF SUMMARY OF THE INVENTION

Plants of the cultivar 'Sunny Henry' have not been observed under all possible environmental conditions. The phenotype may vary somewhat with the variations in environment such as temperature, light intensity, day length, and fertility level without, however, any variance in genotype.

The following traits have been repeatedly observed and are determined to be the unique characteristics of 'Sunny Henry'. The following characteristics in combination distinguish 'Sunny Henry' as a new and distinct cultivar:

1. White ray floret color, RHS 158D, with slight green-yellow tinge, RHS 1B, to pure white, RHS 155D.
2. Dense and bushy plant form, mainly due to more upright stems.
3. Vigorous growth habit; less need for chemical growth retardation.
4. High number of inflorescences per plant.

Plants of the cultivar 'Sunny Henry' can be compared to plants of the parental cultivar '1.154.93'. Plants of the cultivar 'Sunny Henry' differ from plants of the parental cultivar, '1.154.93', primarily in inflorescence color.

Plants of 'Sunny Henry' differ from plants of the parental cultivar, 'Sunny Alex' in the following characteristics described in Table 1:

TABLE 1

| Trait | 'Sunny Henry' | 'Sunny Alex' |
|---|---|---|
| Plant height | 15 cm | 17 cm |
| Width | 18 cm | 17 cm |
| Inflorescence Color | White | Orange-yellow |
| Foliage | Single, obovate to lanceolate | Broadly lobed |

Plants of the cultivar 'Sunny Henry' can be compared to plants of the *Osteospermum ecklonis* (*DC*) *T. Norl.* cultivar 'Sunny Gustav' (U.S. Plant Pat. No. 10,670). In side-by-side comparisons conducted by the Inventor in Stige Denmark, plants of the cultivar 'Sunny Henry' and the cultivar 'Sunny Gustav' differ in the following characteristics:

1. 'Sunny Henry' has striking white ray florets, RHS 155C, and white disk florets, RHS N155D, with orange pollen, while 'Sunny Gustav' has a white flower with blue eye.

2. 'Sunny Henry' has yellow-green-colored leaves while plants of the cultivar 'Sunny Gustav' have darker green leaves.
3. 'Sunny Henry' has shorter peduncles than plants of the cultivar 'Sunny Gustav'.
4. 'Sunny Henry' is shorter and more compact than the plants of the cultivar 'Sunny Gustav'.
5. 'Sunny Henry' has more and larger inflorescences per plant than the plants of the cultivar 'Sunny Gustav'.

BRIEF DESCRIPTION OF THE PHOTOGRAPHS

The accompanying color photographs illustrate the overall appearance of the new *Osteospermum* cultivar 'Sunny Henry' showing the colors as true as is reasonably possible with colored reproductions of this type. Colors in the photographs may differ slightly from the color values cited in the detailed botanical description which accurately describe the color of the new *Osteospermum* cultivar 'Sunny Henry'.

The first photograph comprises a side perspective view of a typical flowering plant of 'Sunny Henry' as grown in an 11 cm pot.

The second photograph is a close-up of the young and older inflorescences of 'Sunny Henry'.

The third photograph is a top view of a typical flowering plant of 'Sunny Henry'.

The fourth photograph shows the inflorescences and leaves of 'Sunny Henry' (in the fourth photograph, 'Sunny Henry' is labelled by its breeder's reference no. '10.514.01').

DETAILED BOTANICAL DESCRIPTION

In the following description, color references are made to The Royal Horticultural Society Colour Chart, 4$^{th}$ edition, where general terms of ordinary dictionary significance are used. Plants were grown under greenhouse conditions. The plants described were grown for about 20 weeks after cutting.

Plant description:

*Form.*—Perennial plant with upright, globular plant habit; composite flower heads; freely branching with lateral flowering branches forming at every node; dense and bushy.

*Crop time.*—After rooting, about 18 weeks are required to produce finished flowering plants in 11 cm pots.

*Plant height* (*soil level to top of plant plane*).—About 15 cm.

*Plant width.*—18 cm.

*Vigor.*—Vigorous growth rate.

*Time to initiate roots.*—About 10 to 14 days at 18 to 21 C in tunnels in a greenhouse.

*Root description.*—Fine, well branched.

*Foliage description.*—Leaves alternate, single, pinnate venation. Length: 3–9 cm. Width: About 30 mm. Shape: Obovate to lanceolate. Apex: obtuse. Base: attenuate. Margin: broadly dentate. Texture: smooth, glabrous, shiny. Scattered short, stiff hairs. Color: Young foliage, upper and lower surfaces: RHS 147B, yellow-green. Mature foliage upper surfaces RHS N147A and lower surface RHS 148A. Venation, RHS 148B.

Inflorescence description:

*Inflorescence arrangement and shape.*—Tubular disk and ray florets in composite daisy heads; with 15 parted involucre.

*Natural flowering season.*—Continuous throughout the spring and summer. Season can be extended by vernalization and long day treatments. Hot weather above 30° C. reduces flowering.

*Inflorescence longevity on the plant.*—Longevity of individual inflorescences is highly dependent on temperature and light conditions 5 to 9 days. Inflorescences persistent, ray florets folding and withering slowly.

*Inflorescence size.*—Diameter about 6 cm.

*Inflorescence depth.*—Typical: 6 mm. Observed: 6 mm.

Inflorescences:

*Ray florets.*—Typical number of ray florets per inflorescence: 22. Observed number of ray florets per inflorescence: 20–24. Length: Ray florets: About 27 mm. Width (diameter): About 8 mm. Ray floret apex: lanceolate, acute. Ray floret base: attenuate. Ray floret margin: entire. Ray floret color: Upper surfaces (when opening): white, RHS 158D, with slight green-yellow tinge, RHS 1B; under sides (when opening): center, RHS 1B, green-yellow, with edges RHS 1D, green-yellow; Upper surfaces (fully opened): white, RHS 155C; under sides (fully opened): RHS 1A, green-yellow, at tip and fading toward base and edges.

*Disk florets.*—Typical number of disks florets per inflorescence: 55. Observed number of disks florets per inflorescence: 50–60,. Length: Disk florets: About 4 mm. Width (diameter): About 2 mm. Disk floret overall shape: tubular. Disk floret apex: attenuate. Disk floret base: fused. Disk floret margin: fused. Disk florets color: RHS N155D, white before anthesis: RHS 156A, greyed-white.

*Peduncle.*—Strength: Moderately strong. Length: About 6 cm. Diameter: About 3 mm. Color: 144C yellow-green.

*Phyllary.*—Typical number of phyllaries: 15. Observed number of phyllaries: 15. Length: 6–12 mm. Width: 1–3 mm. Overall shape: lanceolate. Apex shape: acuminate. Base shape: fused. Margin: entire. Color: Upper surface: RHS 137D, green; lower surface: RHS 137D, green.

Reproductive organs:

*Androecium.*—Location: disc florets only. Anthers: Linear, fused, stamen, color: RHS 17A, yellow-orange. Pollen: Color RHS 17A yellow-orange.

*Gynoecium.*—Location of gynoecium: ray and disc florets. Pistil and stigma: Typical pistil number: 1. Observed pistil number: 1. Stigma color: RHS 16C yellow-orange.

*Seed.*—Length: About 1 mm. Diameter: About 0.3 mm.

Disease/pest resistance: Good.

Disease/pest susceptibility: Low.

Weather tolerance: Plants of the new *Osteospermum* have exhibited good tolerance to draught, rain and wind, and low temperatures to −1° C.

I claim:

1. A new and distinct cultivar of *Osteospermum* plant named 'Sunny Henry', as illustrated and described herein.

* * * * *

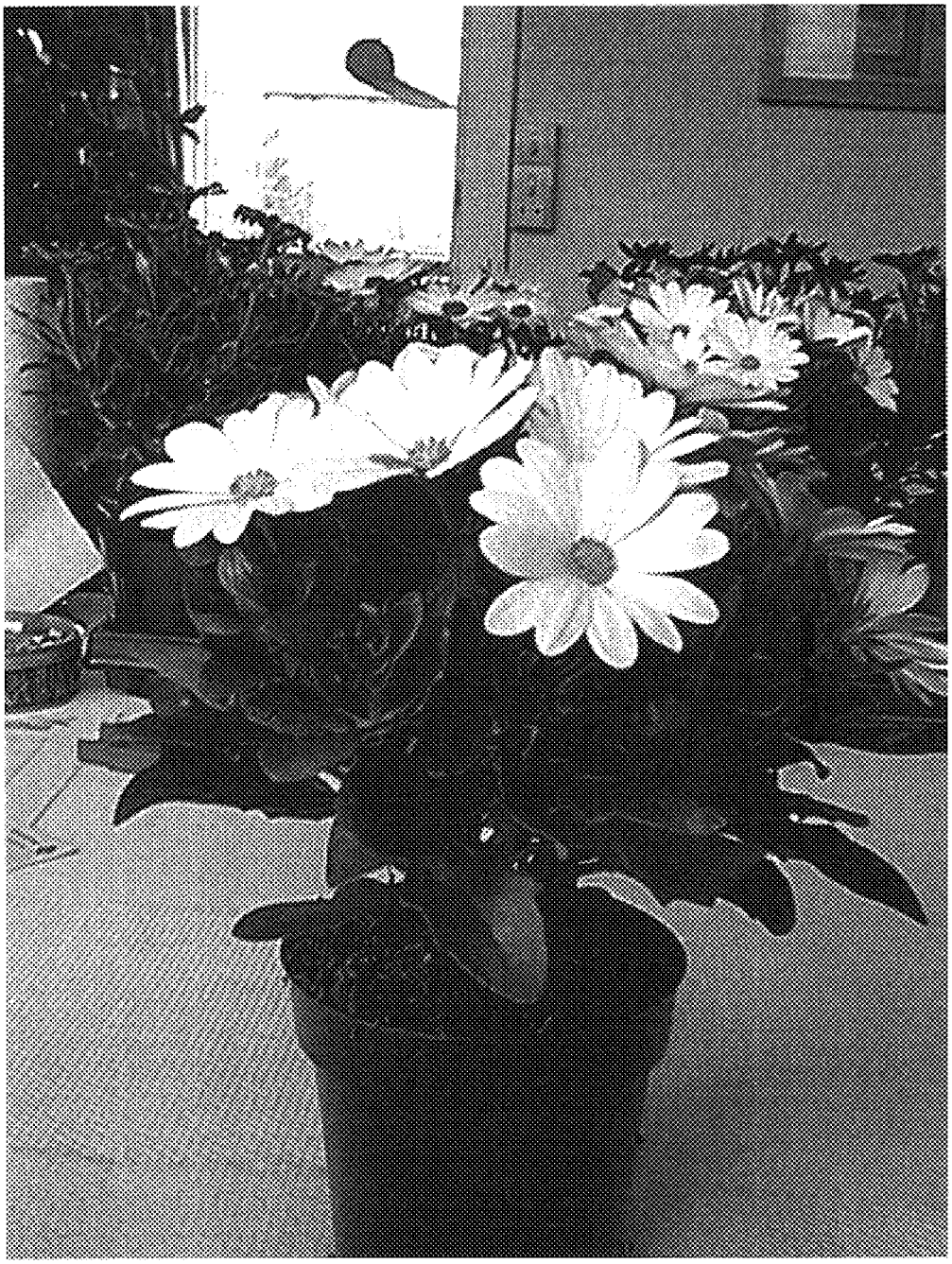

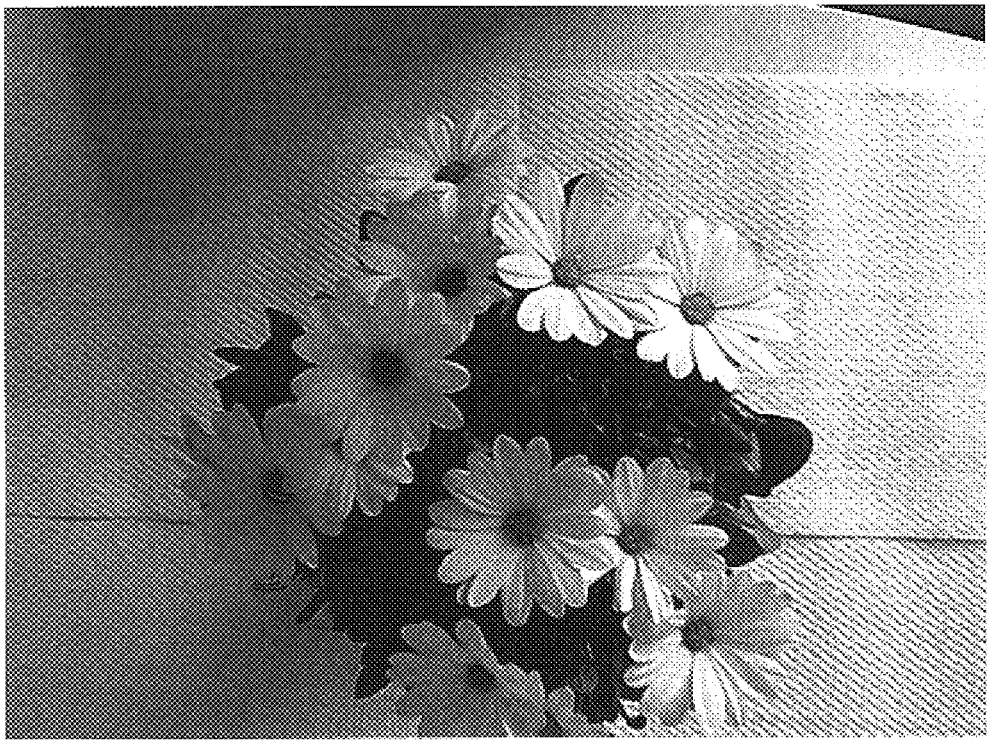

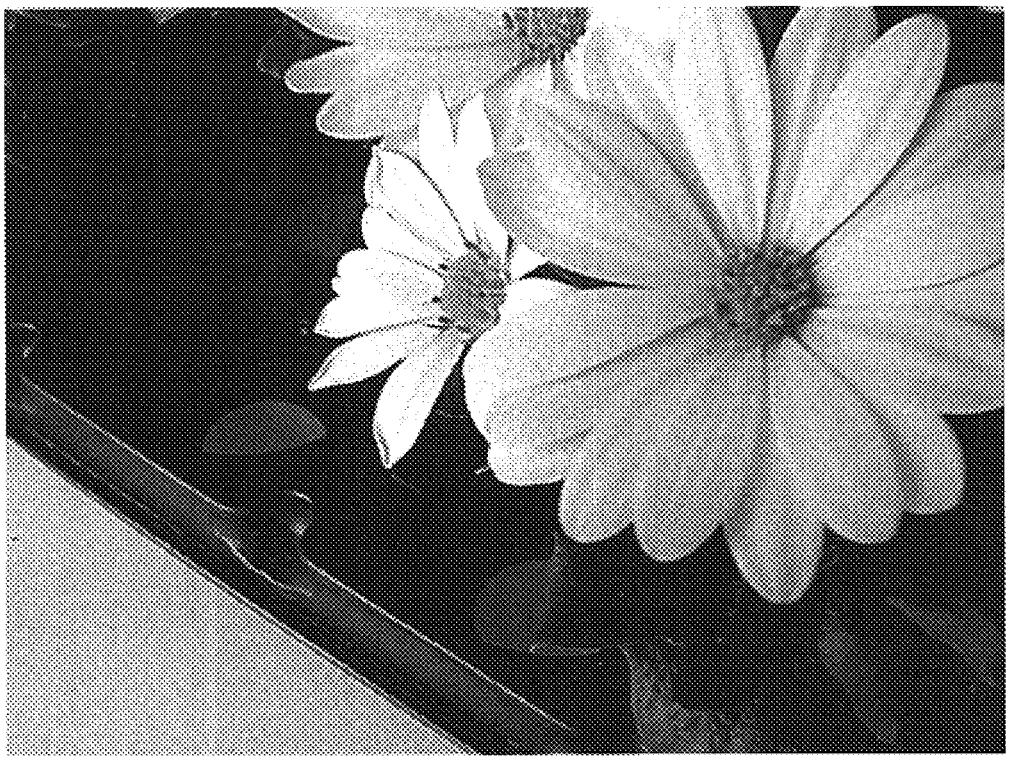

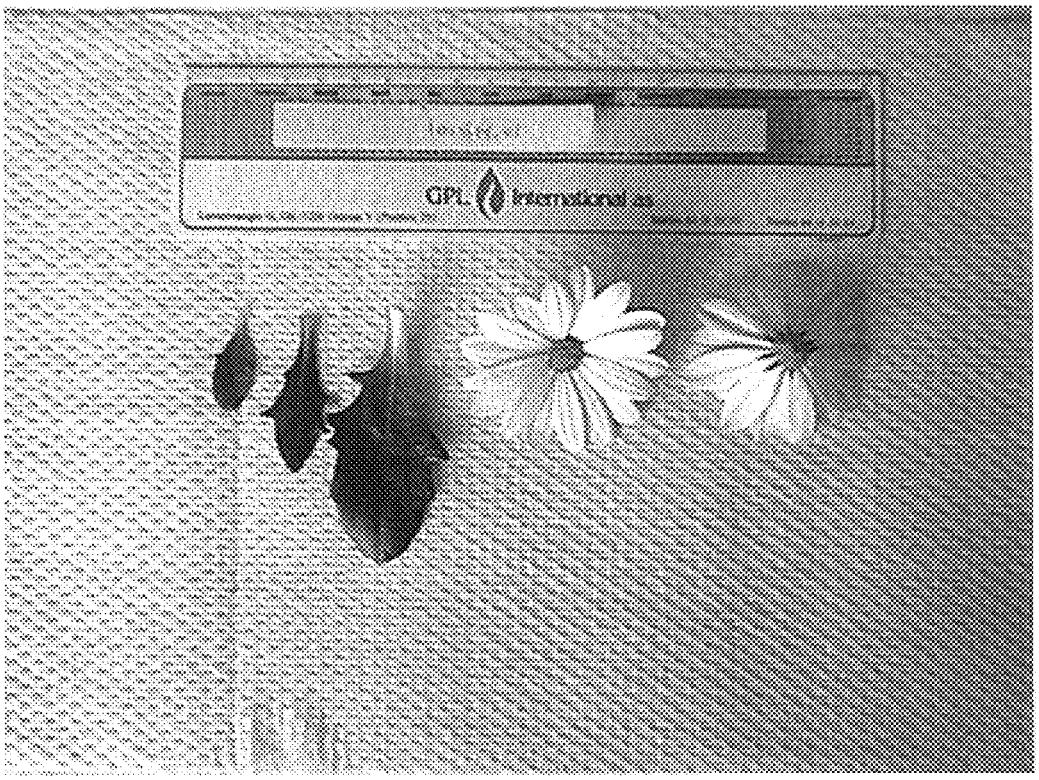
GPL